United States Patent
Althaus et al.

(12) 
(10) Patent No.: US 11,320,439 B2
(45) Date of Patent: May 3, 2022

(54) BINDING ASSAY FOR THE DIAGNOSIS OF A HEPARIN-INDUCED THROMBOCYTOPENIA

(71) Applicant: Siemens Healthcare Diagnostics Products GmbH, Marburg (DE)

(72) Inventors: Harald Althaus, Wetter (DE); Herbert Schwarz, Lohra (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 459 days.

(21) Appl. No.: 16/048,028

(22) Filed: Jul. 27, 2018

(65) Prior Publication Data

US 2019/0041398 A1 Feb. 7, 2019

(30) Foreign Application Priority Data

Aug. 2, 2017 (EP) .................................... 17184389

(51) Int. Cl.
| | | |
|---|---|---|
| *G01N 33/564* | (2006.01) | |
| *G01N 33/566* | (2006.01) | |
| *G01N 33/68* | (2006.01) | |
| *G01N 33/543* | (2006.01) | |

(52) U.S. Cl.
CPC ... *G01N 33/6854* (2013.01); *G01N 33/54313* (2013.01); *G01N 33/564* (2013.01); *G01N 33/566* (2013.01); *G01N 33/6893* (2013.01); *G01N 2800/222* (2013.01); *G01N 2800/226* (2013.01)

(58) Field of Classification Search
CPC ........... G01N 33/54313; G01N 33/564; G01N 33/566
See application file for complete search history.

(56) References Cited

U.S. PATENT DOCUMENTS

| | | | |
|---|---|---|---|
| 3,996,345 A | | 12/1976 | Ullman et al. |
| 5,466,582 A | * | 11/1995 | Amiral .................... G01N 33/94 |
| | | | 435/7.9 |
| 5,763,199 A | * | 6/1998 | Coller ................ G01N 33/5091 |
| | | | 435/7.21 |
| 2004/0175696 A1 | * | 9/2004 | Ullman ................ G01N 33/531 |
| | | | 435/6.12 |
| 2011/0091911 A1 | * | 4/2011 | Halverson .............. G01N 33/80 |
| | | | 435/7.92 |
| 2015/0064800 A1 | * | 3/2015 | Chance .............. G01N 33/6854 |
| | | | 436/501 |
| 2018/0074078 A1 | * | 3/2018 | Aster ................. G01N 33/6854 |

FOREIGN PATENT DOCUMENTS

| | | |
|---|---|---|
| EP | 0515194 | 11/1992 |
| WO | WO-95/06877 | 3/1995 |
| WO | WO-2012/113801 | 8/2012 |

OTHER PUBLICATIONS

Bakchoul, T. et al. (2014). "Current insights into the laboratory diagnosis of HIT." *International Journal of Laboratory Hematology* 36: 296-305.
Cuker, A. et al. (May 2013). "Novel diagnostic assays for heparin-induced thrombocytopenia." *Blood* 121(18): 3727-3732.
Newman, D. J. et al. (1992). "Particle enhanced light scattering immunoassay." *Annals of Clinical Biochemistry* 29: 22-42.
Peula, J. M. et al. (1995). "Covalent coupling of antibodies to aldehyde groups on polymer carriers." *Journal of Materials Science: Materials in Medicine* 6: 779-785.
Udenfriend, S. et al. (Dec. 1985). "Scintillation proximity radioimmunoassay utilizing $^{125}$I-labeled ligands." *Proceedings of the National Academy of Sciences USA* 82: 8672-8676.

* cited by examiner

*Primary Examiner* — Gailene Gabel
(74) *Attorney, Agent, or Firm* — BakerHostetler

(57) ABSTRACT

The present disclosure is in the field of in vitro diagnostics and relates to an easily automatable binding assay for establishing a heparin-induced thrombocytopenia, which binding assay uses FcγRIIa protein-coated particles.

12 Claims, No Drawings

BINDING ASSAY FOR THE DIAGNOSIS OF A HEPARIN-INDUCED THROMBOCYTOPENIA

CROSS-REFERENCE TO RELATED APPLICATIONS

This application claims priority to European Application No. EP17184389.9, filed Aug. 2, 2017, the disclosure of which is hereby incorporated by reference in its entirety.

BACKGROUND OF THE INVENTION

The present invention is in the field of in vitro diagnostics and relates to an easily automatable binding assay for establishing a heparin-induced thrombocytopenia, which binding assay uses FcγRIIa protein-coated particles.

Heparin-induced thrombocytopenia (HIT) is a thrombotic disorder which can arise during a heparin therapy and can cause life-threatening thromboembolic complications. Affected patients produce antibodies which bind a complex composed of heparin and platelet factor 4 (PF4), so-called anti-PF4/heparin complex antibodies. In vivo, the antibody-bound PF4/heparin complex binds to the thrombocyte surface and causes an activation of the thrombocytes. This leads to a reduction in the thrombocyte count and to an increased risk of thromboembolisms.

Two assay principles are mainly used for HIT diagnosis. The first assay principle is based on the direct detection of anti-PF4/heparin complex antibodies in a body-fluid sample from a patient. To this end, a sample is contacted with PF4/heparin complex or a complex composed of PF4 and another suitable polyanion (such as, for example, polyvinyl sulfonate), and the binding of any anti-PF4/heparin complex antibodies present in the sample is detected using conventional immunological assay methods (e.g., ELISA). However, a disadvantage is that, although the detection of anti-PF4/heparin complex antibodies is sensitive, it is not sufficiently specific, i.e., the detection of the antibodies is inadequate for a positive HIT diagnosis, whereas a negative result appropriately reliably rules out a HIT. Therefore, confirmation by a functional assay based on a second assay principle is recommended.

The second, functional assay principle is based on the detection of the thrombocyte-activating action of the anti-PF4/heparin complex antibodies. In said assay principle, washed thrombocytes from one or more normal donors are mixed with a plasma or serum sample from a patient and with heparin, and thrombocyte activation is measured on the basis of known activation markers, such as, for example, on the basis of the amount of released serotonin (serotonin-release assay), or on the basis of the visually identifiable aggregation reaction of the thrombocytes (HIPA assay). If a patient sample contains anti-PF4/heparin complex antibodies, it is possible to establish a thrombocyte activation which is increased compared to a normal sample (without such antibodies).

The thrombocyte-based, functional assays have the disadvantage that the thrombocytes must be prepared in complicated, manual methods and can only be used fresh owing to their insufficient shelf life. In addition, it is always necessary to use a mixture of thrombocytes from multiple donors in order to compensate for biological variations between individual thrombocyte preparations in order to thus allow a certain standardization.

DETAILED DESCRIPTION OF THE INVENTION

It is an object of the present invention to provide a method for detecting anti-PF4/heparin complex antibodies in a body-fluid sample, which method avoids the aforementioned disadvantages, particularly the use of thrombocytes.

It has been found that, in a reaction mixture which by mixing a sample with heparin or PF4/heparin complex and with a particulate solid phase and determination of the agglutination of the particulate solid phase, the presence of anti-PF4/heparin complex antibodies in the sample can be established when the particulate solid phase has been coated with isolated FcγRIIa protein.

The present invention thus provides a method for detecting anti-PF4/heparin complex antibodies in a body-fluid sample. The method comprises the steps:
i. providing a reaction mixture by mixing the sample
   with heparin or a PF4-binding, unbranched polysaccharide or a PF4-binding polyanion, or
   with PF4/heparin complex or a complex composed of PF4 with an unbranched polysaccharide or a polyanion, and
   with a particulate solid phase;
ii. measuring the agglutination of the particulate solid phase in the reaction mixture;
iii. comparing the thus measured agglutination in the reaction mixture with a predetermined reference value for the agglutination in reaction mixtures containing body-fluid samples from donors known to contain no anti-PF4/heparin complex antibodies; and
iv. establishing the presence of anti-PF4/heparin complex antibodies in the sample when the agglutination determined in the reaction mixture exceeds the reference value, wherein the particulate solid phase has been coated with isolated FcγRIIa protein.

The body-fluid sample preferably originates from a person. Preferably, the body-fluid sample is one which is substantially thrombocyte-free and is, in particular, plasma or serum.

The body-fluid sample can be mixed with a PF4-binding, unbranched polysaccharide or with a PF4-binding polyanion. A multiplicity of PF4-binding substances which form with PF4 a complex which is bound by the anti-PF4/heparin complex antibodies to be detected are known. Suitable unbranched polysaccharides are, for example, heparin, unfractionated heparin (UFH), fractionated heparin (LMWH), dextran sulfate and fucoidan. Suitable polyanions are, for example, polyvinyl sulfate, polyvinyl sulfonate, polyvinyl phosphate, polyvinyl phosphonate, polystyrene sulfate and polystyrene sulfonate.

Alternatively, the body-fluid sample can be mixed with PF4/heparin complex or with a complex composed of PF4 with an unbranched polysaccharide or a polyanion.

Furthermore, the sample is mixed with a particulate solid phase which has been coated with isolated FcγRIIa protein.

In the context of this invention, the term "particulate solid phase" is to be understood to mean noncellular particles which have an approximate diameter of at least 20 nm and not more than 20 μm, usually between 200 nm and 350 nm, preferably between 250 and 320 nm, particularly preferably between 270 and 290 nm, very particularly preferably 280 nm. The microparticles can be of regular or irregular shape. They can be spheres, spheroids, spheres with more or less large cavities or pores. The microparticles can consist of organic material, of inorganic material, or of a mixture or a combination of the two. They can consist of a porous or nonporous, a swellable or nonswellable material. In principle, the microparticles can have any density, but preference is given to particles having a density approaching the density of water, such as from about 0.7 to about 1.5 g/ml. The preferred microparticles are suspendable in aqueous solutions and are suspension-stable for as long as possible. They may be transparent, partially transparent or nontransparent. The microparticles can consist of multiple layers such as, for example, the so-called "core-and-shell" particles comprising a core and one or more enveloping layers. The term microparticles encompasses, for example, dye crystals, metal sols, silica particles, glass particles and magnetic particles. Preferred microparticles are particles which are suspendable in aqueous solutions and consist of water-insoluble polymer material, in particular consist of substituted polyethylenes. Very particular preference is given to latex particles, for example composed of polystyrene, acrylic acid polymers, methacrylic acid polymers, acrylonitrile polymers, acrylonitrile butadiene styrene, polyvinyl acetate acrylate, polyvinyl pyridine, vinyl chloride acrylate. Of particular interest are latex particles having reactive groups on their surface, such as, for example, carboxyl, amino or aldehyde groups, which allow covalent bonding of isolated FcγRIIa protein to the latex particles. In the context of this invention, human, animal, plant or fungal cells or bacteria are explicitly not encompassed by the term "particulate solid phase".

The term "isolated FcγRIIa protein" is to be understood to mean a recombinantly or synthetically produced FcγRIIa protein or a native FcγRIIa protein, i.e., from natural sources, purified for example from human leukocytes. Suitable for the production of recombinant FcγRIIa protein are known prokaryotic or eukaryotic expression systems, such as, for example, expression in bacteria (e.g., *E. coli*), in yeasts (e.g., *Saccharomyces cerevisiae, Pichia pastoris*), in plant, animal or human cell cultures. Suitable for the production of synthetic FcγRIIa protein are known techniques for in vitro protein synthesis, such as, for example, solid-phase syntheses (e.g., Merrifield synthesis). Preferably, the FcγRIIa protein used in the method according to the invention is recombinantly produced FcγRIIa protein which was produced in a culture of human cells, preferably in a culture of human embryonic kidney cells (HEK cells).

The FcγRIIa protein (synonym: CD32a protein) is preferably human FcγRIIa protein. The term "FcγRIIa protein" encompasses not only the complete FcγRIIa protein, but also fragments of the complete FcγRIIa protein that are capable of binding to immunocomplexes composed of PF4/heparin complex and anti-PF4/heparin complex antibody bound thereto. The term "FcγRIIa protein" further encompasses not only the wild-type FcγRIIa protein or fragments thereof, but also FcγRIIa proteins having one or more amino acid substitutions that are capable of binding to PF4/heparin complex, such as, for example, a known substitution at position 131 of the human FcγRIIa protein. The FcγRIIa protein or an FcγRIIa protein fragment can be fused at the N-terminus with a heterologous signal sequence, i.e., with a polypeptide which is usually not present in the human FcγRIIa protein, but which positively influences in the selected expression system the expression and/or secretion of the recombinantly expressed FcγRIIa protein. Furthermore, the FcγRIIa protein or an FcγRIIa protein fragment can be fused at the C-terminus with one or more affinity tags which allow the binding of the, for example, recombinantly expressed protein to an affinity support, allowing, for example, the purification of recombinantly expressed FcγRIIa protein. Preference is given to small affinity tags having a length of not more than 12 amino acids. Particular preference is given to affinity tags from the group consisting of His-tag, Flag-tag, Arg-tag, c-Myc-tag and Strep-tag. Suitable affinity supports which bind to an affinity tag with high affinity are, for example, specific antibodies, immobilized cations (e.g., $Ni^{2+}$ with affinity for His-tags) or other types of binding partners (e.g., streptavidin with affinity for Strep-tags).

If the body-fluid sample contains anti-PF4/heparin complex antibodies, these bind in the reaction mixture to PF4/heparin complexes. The immunocomplexes formed are bound by the FcγRIIa protein and bring about an agglutination of the particulate solid phase in the reaction mixture.

The measurement of the agglutination of the particulate solid phase in the reaction mixture can be done photometrically, for example turbidimetrically or nephelometrically. Binding assays based on the principle of particle-enhanced light scattering have been known since about 1920 (for an overview, see Newman, D. J. et al., Particle enhanced light scattering immunoassay. Ann Clin Biochem 1992; 29: 22-42). Preferably, polystyrene particles having a diameter of 0.1 to 0.5 µm, particularly preferably having a diameter of 0.15 to 0.35 µm, are used in this connection. Preferably, polystyrene particles having amine, carboxyl or aldehyde functions are used. Further preferably, shell/core particles are used. The synthesis of the particles and the covalent coupling of ligands is, for example, described in Peula, J. M. et al., Covalent coupling of antibodies to aldehyde groups on polymer carriers. Journal of Materials Science: Materials in Medicine 1995; 6: 779-785.

Alternatively, the measurement of the agglutination of the particulate solid phase in the reaction mixture can be done by measuring a signal which is generated by a signal-forming system when a first and a second component of the signal-forming system are brought into close proximity to one another. In this connection, a first fraction of the particulate solid phase has been associated with a first component of a signal-forming system and a second fraction of the particulate solid phase has been associated with a second component of the signal-forming system, wherein the first and second component of the signal-forming system interact such that a detectable signal is formed when the first and the second component of the signal-forming system are brought into close proximity to one another, and the agglutination of the particulate solid phase in the reaction mixture is measured on the basis of the signal which is formed.

In this embodiment of the method according to the invention, the signal-forming system comprises at least one first and one second component which interact such that a detectable signal is formed when they are brought into close proximity to one another and can interact with one another as a result. An interaction between the components is to be understood to mean in particular an energy transfer, i.e., the direct transfer of energy between the components, for example by light or electron radiation and also via reactive chemical molecules, such as, for example, short-lived singlet oxygen. The energy transfer can take place from one component to another, but a cascade of different substances, across which the energy transfer runs, is also possible. For example, the components can be a pair composed of an energy donor and an energy acceptor, such as, for example, photosensitizer and chemiluminescent agent (EP-A2-0515194, LOCI® technology) or photosensitizer and fluorophore (WO 95/06877) or radioactive iodine<125> and fluorophore (Udenfriend et al. (1985) Proc. Natl. Acad. Sci. 82: 8672-8676) or fluorophore and fluorescence quencher (U.S. Pat. No. 3,996,345). Particularly preferably, the first component of the signal-forming system is a chemiluminescent agent and the second component of the signal-forming system is a photosensitizer or vice versa, and the chemiluminescence in the reaction mixture is measured.

After the agglutination in the reaction mixture has been measured (e.g., by determining the maximum change in absorption for the reaction mixture), the thus measured agglutination is compared with a predetermined reference value. A suitable reference value is the agglutination which is measured (or has been measured beforehand) with the same method in reaction mixtures containing body-fluid samples from donors known to contain no anti-PF4/heparin complex antibodies. Usually, in order to determine a reference value, the agglutination is measured in a multiplicity of samples from healthy donors known to have no anti-PF4/heparin complex antibodies and then compared with the agglutination for a multiplicity of samples from donors suffering from HIT and having anti-PF4/heparin complex antibodies. A reference value can, for example, then be a threshold which allows the differentiation of samples with anti-PF4/heparin complex antibodies and those without. If the agglutination measured in a reaction mixture exceeds the reference value, this makes it possible to establish the presence of anti-PF4/heparin complex antibodies in the sample. By contrast, if the agglutination measured in the reaction mixture falls short of the reference value, this makes it possible to establish the absence of anti-PF4/heparin complex antibodies in the sample.

The present invention further provides a method for diagnosing a heparin-induced thrombocytopenia, wherein a method according to the invention is used to detect the presence of anti-PF4/heparin complex antibodies in a body-fluid sample from a patient.

The present invention additionally further provides an assay kit for carrying out a method according to the invention. The assay kit contains at least the following components:
a. a first reagent containing heparin, a PF4-binding, unbranched polysaccharide or a PF4-binding polyanion or PF4/heparin complex or a complex composed of PF4 with an unbranched polysaccharide or a polyanion; and
b. a second reagent containing a particulate solid phase which has been coated with isolated FcγRIIa protein.

The first reagent can contain
a PF4-binding, unbranched polysaccharide, preferably from the group consisting of heparin, unfractionated heparin, fractionated heparin, dextran sulfate and fucoidan; or
a PF4-binding polyanion, preferably from the group consisting of polyvinyl sulfate, polyvinyl sulfonate, polyvinyl phosphate, polyvinyl phosphonate, polystyrene sulfate and polystyrene sulfonate; or
PF4/heparin complex; or
a complex composed of PF4 with an unbranched polysaccharide or a polyanion.

The first and the second reagent are intended for the provision of the reaction mixture with the body-fluid sample.

In a preferred assay kit, the particulate solid phase present in the second reagent consists of latex particles. Such an assay kit is suitable for the measurement of the agglutination by means of photometric methods.

Another embodiment of the assay kit contains, besides the first and second reagent, additionally a third reagent which likewise contains a particulate solid phase which has been coated with isolated FcγRIIa protein. In this connection, the particulate solid phase of the second reagent has been associated with a first component of a signal-forming system and the particulate solid phase of the third reagent has been associated with a second component of the signal-forming system, wherein the first and second component of the signal-forming system interact such that a detectable signal is formed when the first and the second component of the signal-forming system are brought into close proximity to one another. Preferably, the first component of the signal-forming system is a chemiluminescent agent and the second component of the signal-forming system is a photosensitizer or vice versa. Such an assay kit is suitable for the measurement of the agglutination by means of chemiluminescence measurement.

In yet another embodiment of the assay kit, the heparin, PF4-binding, unbranched polysaccharide or PF4-binding polyanion that is present in the first reagent or the PF4/heparin complex that is present in the first reagent or the complex composed of PF4 with an unbranched polysaccharide or a polyanion has been coupled to a further particulate solid phase, preferably to latex particles.

The reagents of an assay kit according to the invention can be provided in liquid or lyophilized form. If some or all reagents of the assay kit are present as lyophilisates, the assay kit can additionally contain the solvents required to dissolve the lyophilisates, such as, for example, distilled water or suitable buffers.

The following examples serve to illustrate the present invention and are not to be understood as restrictive.

EXAMPLES

Example 1: Homogeneous Binding Assay for the Detection of Anti-PF4/Heparin Complex Antibodies Reagent 1 was prepared by mixing PF4 protein isolated from human thrombocyte concentrate with unfractionated heparin (UFH) in a ratio of 10 μg of PF4 protein:0.2 U/mL (UFH) in a buffer solution. Alternatively, a Reagent 1 containing only unfractionated heparin (UFH) (0.2 U/mL) was used.

Reagent 2 was prepared by mixing and incubating about 1 mg of human FcγRIIa protein with 1 mL of polystyrene latex particles (50 mg/mL, particle diameter 0.2-0.3 μm) in a buffer solution. After repeated washing of the particles, the particles were then resuspended in 50 mL of a buffer solution.

20 μL of a human serum sample were mixed with 20 μL of Reagent 1 containing PF4/heparin complex and 80 μL of Reagent 2 containing FcγRIIa protein-coated latex particles to form a reaction mixture and incubated at 37° C.

The optical density (OD) of the reaction mixture was measured in a BCS XP analyzer (Siemens Healthcare Diagnostics Products GmbH) at a wavelength of 570 nm for a period of 6 minutes, and the mean change in optical density per minute (Delta OD/min) was ascertained as the measurement result.

The agglutination assay according to the invention was used to measure serum samples from 5 HIT patients, for whom a HIT had been diagnosed on the basis of clinical criteria (4T score, in some cases with thrombotic event) and the existence of anti-PF4/heparin complex antibodies had been established using two independent, commercially available immunoassays (HemosIL® AcuStar HIT-Ab(PF4-H), Instrumentation Laboratories, and Asserachrom® HPIA-IgG, Diagnostica Stago).

Furthermore, serum samples from 4 healthy donors (who did not have clinical HIT criteria and also did not have anti-PF4/heparin complex antibodies) and a normal plasma pool (from about 20 plasmas from healthy donors, "FNP") were measured.

Buffer was used as negative control.

The assay results are compiled in Table 1. There is a distinction between assay results using either Reagent 1 containing PF4/heparin complex (PF4/Heparin) or Reagent 1 containing only heparin (Heparin).

TABLE 1

Results of the agglutination assay according to the invention for HIT diagnosis

| | Sample ID | PF4/Heparin Delta OD/min [570 nm] | Heparin Delta OD/min [570 nm] |
|---|---|---|---|
| Healthy donors | N 050 | 0.038 | 0.021 |
| | N 048 | 0.026 | 0.025 |
| | N 038 | 0.041 | 0.063 |
| | N 001i | 0.054 | 0.043 |
| | FNP | 0.025 | 0.027 |
| | Negative control | 0.024 | 0.022 |
| HIT patients | 175390366 | 0.462 | 0.212 |
| | 47288928 | 0.457 | 0.247 |
| | 175419732 | 0.493 | 0.531 |
| | 66793 | 0.344 | 0.271 |
| | 74850 | 0.269 | 0.408 |

It is found that the results of the two agglutination assays according to the invention make it possible to differentiate healthy, HIT-negative blood donors from HIT-positive patients. In all the reaction mixtures containing HIT patient samples, it is possible to measure an agglutination which is significantly elevated compared to healthy donors. As threshold (cut-off) for the differentiation of samples containing anti-PF4/heparin complex antibodies from those containing none, it would be possible to select a Delta OD/min [570 nm] of 0.1 in the two present assay systems.

However, for a statistically more precise definition of the cut-off value, a distinctly higher number of sample measurements is required.

Embodiments

1. A method for detecting anti-PF4/heparin complex antibodies in a body-fluid sample, the method comprising the steps:
   i. providing a reaction mixture by mixing the sample
      with heparin or a PF4-binding, unbranched polysaccharide or a PF4-binding polyanion, or
      with PF4/heparin complex or a complex composed of PF4 with an unbranched polysaccharide or a polyanion, and
      with a particulate solid phase; and
   ii. measuring the agglutination of the particulate solid phase in the reaction mixture;
   iii. comparing the thus measured agglutination in the reaction mixture with a predetermined reference value for the agglutination in reaction mixtures containing body-fluid samples from donors known to contain no anti-PF4/heparin complex antibodies; and
   iv. establishing the presence of anti-PF4/heparin complex antibodies in the sample when the agglutination determined in the reaction mixture exceeds the reference value,
   characterized in that
   the particulate solid phase has been coated with isolated FcγRIIa protein.

2. The method of Embodiment 1, wherein the agglutination of the particulate solid phase in the reaction mixture is measured photometrically.

3. The method Embodiment 1, wherein a first fraction of the particulate solid phase has been associated with a first component of a signal-forming system and a second fraction of the particulate solid phase has been associated with a second component of the signal-forming system, and wherein the first and second component of the signal-forming system interact such that a detectable signal is formed when the first and the second component of the signal-forming system are brought into close proximity to one another, and the agglutination of the particulate solid phase in the reaction mixture is measured on the basis of the signal which is formed.

4. The method Embodiment 3, wherein the first component of the signal-forming system is a chemiluminescent agent and the second component of the signal-forming system is a photosensitizer or vice versa, and wherein the chemiluminescence in the reaction mixture is measured.

5. A method for diagnosing a heparin-induced thrombocytopenia, wherein a method of any of Embodiments 1 to 4 is used to detect the presence of anti-PF4/heparin complex antibodies in a body-fluid sample from a patient.

6. An assay kit for carrying out a method of any of Embodiments 1 to 5, containing the following components:
   a. a first reagent containing heparin, a PF4-binding, unbranched polysaccharide or a PF4-binding polyanion or PF4/heparin complex or a complex composed of PF4 with an unbranched polysaccharide or a polyanion; and
   b. a second reagent containing a particulate solid phase which has been coated with isolated FcγRIIa protein.

7. The assay kit Embodiment 6, further containing the following component:
   c. a third reagent containing a particulate solid phase which has been coated with isolated FcγRIIa protein,
   wherein the particulate solid phase of the second reagent has been associated with a first component of a signal-forming system and the particulate solid phase of the third reagent has been associated with a second component of the signal-forming system, and wherein the first and second component of the signal-forming system interact such that a detectable signal is formed when the first and the second component of the signal-forming system are brought into close proximity to one another.

8. The assay kit of Embodiment 7, wherein the first component of the signal-forming system is a chemiluminescent agent and the second component of the signal-forming system is a photosensitizer or vice versa.

9. The assay kit of any of Embodiments 6 to 8, wherein the particulate solid phase are latex particles.

10. The assay kit of any of Embodiments 6 to 9, wherein the heparin, PF4-binding, unbranched polysaccharide or PF4-binding polyanion that is present in the first reagent or the PF4/heparin complex that is present in the first reagent or the complex composed of PF4 with an unbranched polysaccharide or a polyanion has been coupled to a further particulate solid phase, preferably to latex particles.

What is claimed:

1. A method for detecting anti-platelet factor 4 (PF4)/heparin complex antibodies in a body-fluid sample that is substantially thrombocyte-free, the method comprising the steps:
   i. providing a reaction mixture by mixing the body-fluid sample with heparin;
      a PF4-binding unbranched polysaccharide;
      a PF4-binding polyanion;
      a PF4/heparin complex;
      a complex comprising PF4 and an unbranched polysaccharide; or a complex comprising PF4 and a polyanion; and
a non-cellular particulate solid phase;
ii. measuring agglutination of the particulate solid phase in the reaction mixture;
iii. comparing the measured agglutination in the reaction mixture with a predetermined reference value for the agglutination in reaction mixtures containing body-fluid samples from donors known to contain no anti-PF4/heparin complex antibodies; and
iv. establishing the presence of anti-PF4/heparin complex antibodies in the sample when the agglutination determined in the reaction mixture exceeds the reference value,
wherein the non-cellular particulate solid phase has been coated with isolated fragment crystallizable receptor gamma IIa (FcγRIIa) protein.

2. The method of claim 1, wherein the agglutination of the non-cellular particulate solid phase in the reaction mixture is measured photometrically.

3. The method of claim 1, wherein a first fraction of the non-cellular particulate solid phase has been associated with a first component of a signal-forming system and a second fraction of the non-cellular particulate solid phase has been associated with a second component of the signal-forming system, and wherein the first and second component of the signal-forming system interact such that a detectable signal is formed when the first and the second component of the signal-forming system are brought into close proximity to one another, and the agglutination of the non-cellular particulate solid phase in the reaction mixture is measured on the basis of the signal which is formed.

4. The method of claim 3, wherein the first component of the signal-forming system is a chemiluminescent agent and the second component of the signal-forming system is a photosensitizer, and wherein the chemiluminescence in the reaction mixture is measured.

5. The method of claim 3, wherein the first component of the signal-forming system is a photosensitizer and the second component of the signal-forming system is a chemiluminescent agent, and wherein the chemiluminescence in the reaction mixture is measured.

6. A method for diagnosing a heparin-induced thrombocytopenia, wherein the method of claim 1 is used to detect the presence of anti-PF4/heparin complex antibodies in a body-fluid sample that is substantially thrombocyte-free from a patient.

7. An assay kit for carrying out the method of claim 1, comprising:

a. a first reagent comprising:
heparin;
a PF4-binding unbranched polysaccharide;
a PF4-binding polyanion;
a PF4/heparin complex;
a complex comprising PF4 and an unbranched polysaccharide; or
a complex comprising PF4 and a polyanion; and
b. a second reagent comprising a non-cellular particulate solid phase which has been coated with isolated fragment crystallizable FcγRIIa protein.

8. The assay kit of claim 7, further comprising:
c. a third reagent containing a non-cellular particulate solid phase coated with isolated fragment crystallizable FcγRIIa protein, wherein the non-cellular particulate solid phase of the second reagent has been associated with a first component of a signal-forming system and the non-cellular particulate solid phase of the third reagent has been associated with a second component of the signal-forming system, and wherein the first and second component of the signal-forming system interact such that a detectable signal is formed when the first and the second component of the signal-forming system are brought into close proximity to one another.

9. The assay kit of claim 8, wherein the first component of the signal-forming system is a chemiluminescent agent and the second component of the signal-forming system is a photosensitizer.

10. The assay kit of claim 8, wherein the first component of the signal-forming system is a photosensitizer and the second component of the signal-forming system is a chemiluminescent agent.

11. The assay kit of claim 7, wherein the non-cellular particulate solid phase comprises latex particles.

12. The assay kit of claim 7, wherein
the heparin,
the PF4-binding unbranched polysaccharide,
the PF4-binding polyanion,
the PF4/heparin complex,
the complex comprising PF4 and the unbranched polysaccharide, or
the complex comprising PF4 and the polyanion
that is present in the first reagent is coupled to a further non-cellular particulate solid phase comprising latex particles which has been coated with isolated fragment crystallizable FcγRIIa.

* * * * *